United States Patent [19]

Chatterjee et al.

[11] Patent Number: 5,082,784
[45] Date of Patent: Jan. 21, 1992

[54] CLONED KPNI RESTRICTION-MODIFICATION SYSTEM

[75] Inventors: Deb K. Chatterjee; Alan W. Hammond, both of Gaithersburg, Md.

[73] Assignee: Life Technologies, Inc., Gaithersburg, Md.

[21] Appl. No.: 496,283

[22] Filed: Mar. 20, 1990

[51] Int. Cl.⁵ .................. C12N 1/21; C12N 15/70; C12N 15/55; C07H 19/10
[52] U.S. Cl. ................. 435/252.3; 435/320.1; 435/199; 435/193; 536/27
[58] Field of Search .......... 435/199, 193, 320.1, 435/252.3; 536/27

[56] References Cited

PUBLICATIONS

Tomassini, T. et al., (1978), Nuc. Acids Res. 5(11), 4055–4064.
Mann et al., Cloning of Restriction and Modification Genes in *E. coli*: The HhaII System from Haemophilus Haemolyticus, *Gene*, 3:97–112 (1978).
Brooks et al., Cloning the BamHI Restriction Modification System, *Nucleic Acids Research*, 17:(3) 979–997 (1989).
Howard et al., Cloning the DdeI Restriction-Modification System Using a Two-Step Method, *Nucleic Acids Research*, 14:(20) 7939–7951 (1986).
Szomolanyi et al., Cloning the Modification Methylase Gene of Bacillus Sphaericus R in *Escherichia coli*, *Gene*, 10:219–225 (1980).
Wilson, G., Cloned Restriction-Modification Systems–A Review, *Gene*, 74:281–289 (1988).
Rodicio et al., Cloning and Expression of the SalI Restriction-Modification Genes of Streptomyces Albus G, *Mol. Gen. Genet.*, 213: 346–353 (1988).

*Primary Examiner*—Charles L. Patterson
*Attorney, Agent, or Firm*—Sterne, Kessler, Goldstein & Fox

[57] ABSTRACT

The present invention discloses the cloning and expression in a host such as *Escherichia coli* of the KpnI restriction-modification system from *Klebsiella pneumoniae*, utilizing a two step protocol. Initial protection of the *E. coli* host with methylase expressed on a vector was required to stabilize a compatible vector carrying both the endonuclease and the methylase genes on a single DNA fragment. A chromosomal map was generated localizing the genes for KpnI methylase and endonuclease. An *E. coli* strain was constructed which produced several thousand-fold higher levels of KpnI endonuclease than the level produced by *Klebsiella pneumoniae*. This invention is also directed to cloning and expression of genes encoding for restriction endonuclease isoschizomers of KpnI and/or modification methylase isoschizomers of KpnI methylase.

5 Claims, 3 Drawing Sheets

```
CCCGAGTATA TGCATATGTT TTCATTACCA CCTCCTTTTC CTATTATATA    50
CTAAAAGTGA GATGTGTAAA TAAAATAAAT TATTTGATGG CATTAAAAGT   100
GATAAAAAGC TACACATATC CCTAGCTCGT TTAGAGAGGA AGGGATATAT   150
GATAGTATTA GTGAAGTTTG TTAATATTTA ATTATCTTTT CAATCCATAA   200
TAATTCAAAA GAAACTCTAA AGCATCATTC TTTTGTTTCT CATTTACTGA   250
CTGCAATATA CCAATGACAT TTATTTTCCC ATTATTTGAA TCCCAATAAT   300
TTTTTTTCAT AACTTGATGA CGTCCACACA ATGCTTGCCA CATTTTAGGA   350
TCATTTACAT CAGTTGCGGG ATCTATTGAA TGAGGTGTCA TATGGTCTGG   400
TGTTAGTTTG ACCGTGCCTC CCCCTATAGG ATCAATATCA CCTTCAACTA   450
ACCCACAGTG TTGACCATCT TCCTGCCACT CGCAAGAGTA ATTAGCTCTA   500
TCCAAAACCT GTTCCCAGGT TTCTTTTGTC GGTAATACAC GCTTTGCTGC   550
CTTTGGGCGT CTTGTTGCGT GTGGCATTAT ATACTCTTGC GGAGCTAAAA   600
CCTTCATATC CCGCCAGGAT AAAATAGTAT ATCCTTTATC AGTTCGTAGT   650
TCTGAAAGTC TCTGATGCCA ATTTTCTGGT TGTTTCCCTG TTTTTGGATC   700
AGTTGCCGCC CTAATGATTT GCTGACGAGT TACAACTTTG CCAAGGTTAT   750
TAAGAAATAG GGCTTCAATA CGCTGACTTA CAGTTTTTTG GTCATAACTA   800
TTATTATCAT CACTATAAAC TTTATCAAAG ACATCCATTT GATACCTCCT   850
TTCATTAACC ATCAAACATT ACATTGCCAC ATTTTCATTA AATTTTAAAG   900
GGAATTCTGC AATTTATAAA TCACATCATA ATTGAATAAA ATTTCAACAT   950
GGCTATTTTC AATGATTATC ACTTATTGTA TAATATAAAA ATAATAGGAG  1000
GGTACATGGA TAATCATGCT AACGAAATAA ATAAACTAAG CCGCGAGCTT  1050
GGCCTTTTAT CAAATTACGA ATTCAATATG GATGAACTTA AAAATTTATC  1100
GCCATTGGAT TCTACTAGCT CATCAATTTA TATAGGTGAT AATCTTACCT  1150
ACCTTCAGGG ACTTTCAAAA ACCAGTCCAA AGACCATTGA TTTTTGCTAT  1200
ATTGATCCTC CTTACAATAC AGGCAATAAA ATCATATATC ATGATAACCG  1250
GAAATCAGTT TCCTCTGATA TTTTTGGTTT ACATAACGAA TGGATGTCAT  1300
TTTTGCTTCC AAGACTTTTT CATGCACATA AAATGCTAAA AGATACAGGC  1350
ATTATTGCTA TCAGCATTGA TGACTATGAA TTTGCTCATT TAAAAATACT  1400
GATGGATAAA ATTTTCGGTG AAGATAATTT CATCGGAAAT ATCGTCGTTT  1450
GTCGTTCAAA AAATGGAAAA GGCAGCAAGC GAAATATAGC GTCTGCTCAT  1500
GAATATTTAC TGGTTTATGG AAAATCAGAT ATGGCGGAAC TATCTGGACA  1550
ACCAGATGAT AAATCTCTTT ATGATAAAGT TGATTGTTTT GGTGAATATA  1600
GAATTGACGG AATGTTCAGA AAAAAGGTG ATTCAAGTTT GAGAACTGAT  1650
CGCCCTAATA TGTTTTATCC TTTATATTTT AACCCATCAA CAGGTGAAGT  1700
ACAGGTAGAG CCAGAACTTG GTTAAAAAC AGTCTATCCA ATCGATTCAA  1750
AAGGGATTGA ACGGAGATGG TTATGGAGTA AAGAAACAGC ACGAGAACGC  1800
TCTTGGGAAT TGTTTGCTAG CAAGAACGGT GTAGTTTATG TTAAAAACTA  1850
TTCATCTTCT CATAAACGGA TTAAAGTCAG AACTCTCTGG AATGATAGTT  1900
CTTTTTATAC TGAGAGAGCG ACGAACGAAA TTACAAAAAT ATTTGGCTCA  1950
AAGGTATTTG ATACCCCTAA AGCCCTAAAT TATATTATGT CTATAATTAA  2000
TTGCATGGCA AAACCTGACG CATTAATCCT TGATTTCTTT GCCGGTTCCG  2050
GAACGACATG CTCATGCTGC GGCTGTTCTA AATAGCCTAG ATGGTGGTTC  2100
AAGAAAAACG ATCTTAATGG AAAGCAATCA TCCGATTACT AAGACACACA  2150
TTGCATATAA ATCCGGCTTT AGAAAAATAT CGGATATAAC CATATCGAGA  2200
TTGAATTATG TTTCGGATAA TTTTCCGGAT TTTAAATATA AAAAAATAGA  2250
AATAATATAG CAAATATTTA AAATTAAGCC GCGGTGAGAT CACGCTCGGT  2300
TTGTAATGAA AAGCTT                                       2316
```

FIG. 3

CLONED KPNI RESTRICTION-MODIFICATION SYSTEM

FIELD OF THE INVENTION

The present invention is in the field of genetic engineering and molecular biology. It concerns production of proteins, specifically the KpnI restriction endonuclease and/or modification methylase, in a heterologous organism from a gene carried by a recombinant DNA molecule. This invention is also directed to cloned restriction endonuclease and modification methylase isoschizomers of these enzymes.

BACKGROUND OF THE INVENTION

Restriction endonucleases are a class of enzymes that occur naturally in prokaryotic and eukaryotic organisms. When they are purified away from other contaminating cellular components, restriction endonucleases can be used in the laboratory to cleave DNA molecules into precise fragments. This property enables DNA molecules to be uniquely identified and to be fractionated into their constituent genes. Restriction endonucleases have proved to be indispensable tools in modern genetic research. They are the biochemical "scissors" by means of which genetic engineering and analysis are performed.

Restriction endonucleases act by recognizing and binding to particular sequences of nucleotides (the "recognition sequence") along the DNA molecule. Once bound, they cleave the molecule within, or to one side of, this sequence. Different restriction endonucleases have affinity for different recognition sequences. About 100 kinds of different endonucleases have so far been isolated from many microorganisms, each being identified by the specific base sequence it recognizes and by the cleavage pattern it exhibits. In addition, a number of restriction endonucleases, called restriction endonuclease isoschizomers, have been isolated from different microorganisms which in fact recognize the same recognition sequence as those restriction endonucleases that have previously been identified. These isoschizomers, however, may or may not cleave the same phosphodiester bond as the previously identified endonuclease.

In nature, restriction endonucleases play a protective role in the welfare of the microbial cell. They enable the microorganism to resist infection by foreign DNA molecules like viruses and plasmids that would otherwise destroy or parasitize them. They achieve this resistance by scanning the lengths of the infecting DNA molecule and cleaving them each time that the recognition sequence occurs. The DNA cleavage that takes place disables many of the infecting genes and renders the DNA susceptible to further degradation by nonspecific exonucleases.

A second component of microbial protective systems are the modification methylases. Modification methylases are complementary to their corresponding restriction endonucleases in that they recognize and bind to the same recognition sequence. Modification methylases, in contrast to restriction endonucleases, chemically modify certain nucleotides within the recognition sequence by addition of a methyl group. Following this methylation, the recognition sequence is no longer bound or cleaved by the restriction endonuclease. The microbial cell modifies its DNA by virtue of its modification methylases and therefore is completely insensitive to the presence of its endogenous restriction endonucleases. Thus, endogenous restriction endonuclease and modification methylase provide the means by which a microorganism is able to identify and protect its own DNA, while destroying unmodified foreign DNA.

The combined activities of the restriction endonuclease and the modification methylase are referred to as the restriction-modification system. Three types of restriction-modification systems have been identified that differ according to their subunit structure, substrate requirements and DNA cleavage. Specifically, Type-I and Type-III restriction systems carry both modification and ATP-requiring restriction (cleavage) activity in the same protein. Type-II restriction-modification systems, on the other hand, consist of a separate restriction endonuclease and modification methylase, i.e., the two activities are associated with independent proteins.

Type II restriction endonucleases are endodeoxyribonucleases which are commonly used in modern genetic research. These enzymes recognize and bind to particular DNA sequences and once bound, cleave within or near this recognition sequence. Phosphodiester bonds are thereby hydrolyzed in the double stranded DNA target sequence, i.e., one in each polynucleotide strand. Type-II restriction endonucleases can generate staggered breaks within or near the DNA recognition sequence to produce fragments of DNA with 5' protruding termini, or DNA fragments with 3' protruding termini. Other Type-II restriction endonucleases which cleave at the axis of symmetry, produce blunt ended DNA fragments. Therefore, Type-II restriction endonucleases can differ according to their recognition sequence and/or the location of cleavage within that recognition sequence.

Type-II restriction endonucleases are frequently used by the genetic engineers to manipulate DNA in order to create novel recombinant molecules. Specific Type-II restriction endonucleases are known for numerous DNA sequences, but there is still a need to provide improved means for producing Type-II restriction endonucleases. Therefore, it is an object of the present invention to make commercial production of these enzymes more practical by using recombinant DNA technology.

There has been much effort to clone type II restriction-modification systems. The first cloning of a DNA endonuclease gene was described by Mann MB et al. (1978) Gene 3:97-112. Since then more than seventy DNA methylase and restriction endonucleases have been cloned, the majority of the restriction endonuclease genes being closely linked to its corresponding methylase gene. Cloning of such genes allows one to produce large quantities of an enzyme.

Several methods by which restriction-modification systems can be cloned have been described. A number of endonuclease and methylase genes have been cloned from endogenous plasmids: EcoRII (Kosykh VB et al. (1980) Mol. Gen. Genet. 178:717-718), EcoRI (Newman AK et al. (1981) J. Biol. Chem. 256:2131-2139, and Greene PJ et al. (1981) J. Biol. Chem. 256:2143-2153), EcoRV (Bougueleret L et al. (1984) Nucl. Acids Res. 12:3659-3676), PvuII (Blumenthal RM et al. (1985) J. Bacteriol. 164:501-509), and PaeR71 (Gingeras TR and Brooks JE (1983) Proc. Natl. Acad. Sci. USA 80:402-406) Other methods of cloning include a phage restriction method in which bacterial cells carrying cloned restriction and modification genes will survive phage infection (Mann et al. supra; Walder RY et al. (1981) Proc. Natl. Acad. Sci. U.S.A. 78:1503-1507; and Rodicio MR and Chater KF (1988) Mol. Gen. Genet. 213:346-353), and a procedure based on methylation protection suggested by Mann et al., supra. and Szomolanyi E et al. (1980) Gene 10:219-225. This latter scheme involves digestion of a plasmid library with the restriction enzyme to be cloned so that only plasmids whose sequences are modified, because of the presence of the methylase, will produce transformants in a suitable host. This selection has worked well to clone endonuclease and methylase genes together as well as methylase genes alone (Szomolanyi et al., supra: Janulaitis A et al. (1982) Gene 20:197-204; Walder RY et al. (1983) J. Biol. Chem. 258:1235-1241; Kiss A and Baldanf F (1983) Gene 21:111-119; and Wilson GG (1988) Gene 74:281-289). However, this technique sometimes yields only the methylase gene, even though the endonuclease and modifying genes are closely linked.

Cloning of certain restriction-modification systems in E. coli. including DdeI (Howard KA et al. (1989) Nucl. Acids Res. 14:7939-7950), BamHI (Brooks JE et al. (1989) Nucl. Acids Res. 17:979-997), and KpnI (disclosed herein), has required a multi-step approach. In each case, protection of the host with methylase expressed on a plasmid was necessary to stabilize a compatible vector containing the functional endonuclease gene. A head-start model to explain why some restriction-modification systems must be cloned utilizing a protected host was proposed by Wilson; supra. This model states that in order to establish a plasmid carrying a restriction-modification system, methylase protection must be faster than endonuclease digestion. Otherwise, restriction enzyme would cleave unmethylated plasmid and/or genomic DNA thereby killing the host. Although this model is a plausible explanation of plasmid establishment, it has not been determined previously whether continued independent expression of methylase from a separate plasmid is necessary to maintain the plasmid carrying the restriction-modification system during cell growth and replication.

SUMMARY OF THE INVENTION

The present invention discloses the cloning and expression in a host such as E. coli, of the KpnI type II restriction-modification system utilizing a two step protocol. Initial protection of the host by methylase was required for the establishment of a vector containing the KpnI restriction and modification genes on a common fragment, but not for its maintenance. This invention is also directed to cloned restriction endonuclease and modification methylase isoschizomers of the KpnI restriction-modification system.

The genes encoding the KpnI restriction-modification system from Klebsiella pneumoniae were cloned and expressed in Escherichia coli. The KpnI restriction endonuclease recognizes and cuts the double stranded DNA recognition sequence:

5' G GTAC C 3'

3' C CATG G 5' between the C residues, producing a four-base 3' extension (" " indicates the site of cleaving). The KpnI methylase recognizes and chemically modifies this double stranded DNA sequence such that the resulting modified sequence is resistant to cleavage with its corresponding restriction endonuclea i.e., KpnI. However, the exact site of methylation with KpnI methylase is unknown. Although the endonuclease and methylase genes were closely linked, initial attempts using a prior method to clone both genes as a single DNA fragment in a plasmid vector resulted in deletions spanning all or part of the gene coding for the restriction enzyme. Initial protection of the E. coli host with methylase expressed on a plasmid was required to stabilize a compatible plasmid carrying both the endonuclease and the methylase genes on a single DNA fragment. A chromosomal map was generated localizing the genes for KpnI methylase and endonuclease, respectively, to 1.7 kilobase pair (kb) and 3.5 kb regions denoted in FIG. 2 as "M" and "R" regions, respectively. An E. coli strain, AH29, was constructed which contained two compatible plasmids: an inducible plasmid carrying the KpnI endonuclease gene which amplifies copy number at elevated temperatures, and a pBR322 derivative expressing KpnI methylase. This strain produces approximately 10 million units of KpnI endonuclease per gram wet weight cells. This is several thousand-fold higher than the level of KpnI produced by Klebsiella pneumoniae.

BRIEF DESCRIPTION OF THE DRAWINGS

FIG. 3 presents sequence data for the cloned region of DNA having the KpnI restriction endonuclease and methylase genes. Sites discussed in the text are indicated in bold.

DEFINITIONS

Figure 1:
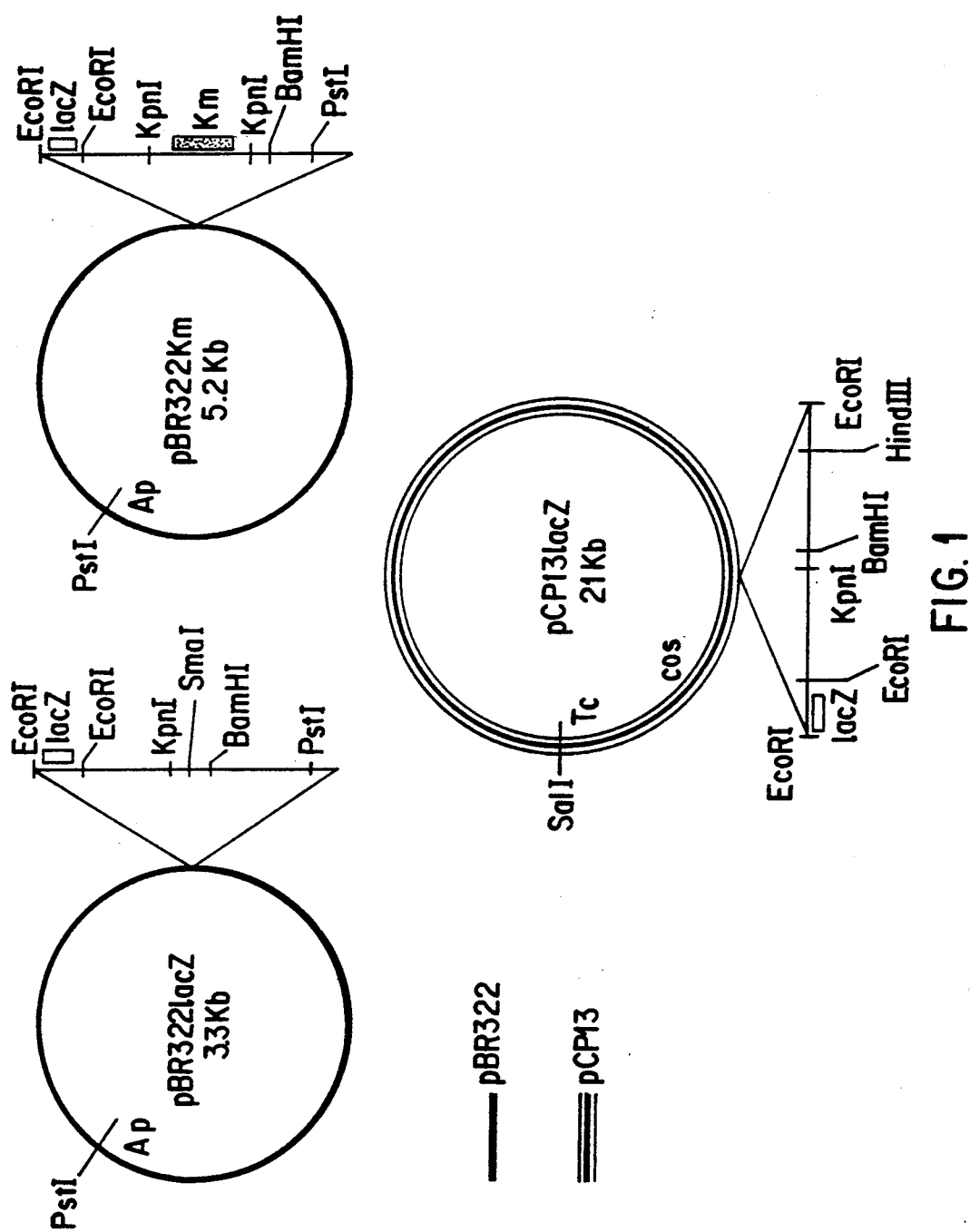
FIG. 1 presents plasmid maps of pBR322lacZ, pBR322Km and pCP13lacZ. Construction of these plasmids is described in Example 1.3. Sequences corresponding to pBR322 and pCP13 are defined in the figure key. The functional lacZ gene in pBR322lacZ and pCP13lacZ allows recombinant selection utilizing the blue/white screen on media containing X-gal. The kanamycin resistance gene in pBR322Km inactivated the lacZ α peptide.

In the description that follows, a number of terms used in recombinant DNA (rDNA) technology are extensively utilized. In order to provide a clear and consistent understanding of the specification and claims, including the scope to be given such terms, the following definitions are provided.

Cloning vector. A plasmid or phage DNA or other DNA sequence which is able to replicate autonomously in a host cell, and which is characterized by one or a small number of endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Expression vector. A vector similar to a cloning vector but which is capable of enhancing the expression of a gene which has been cloned into it, after transformation into a host. The cloned gene is usually placed under the control of (i.e., operably linked to) certain control sequences such as promoter sequences.

Restriction endonuclease isoschizomer. A restriction endonuclease isoschizomer is a term used to designate a group of restriction endonucleases that recognize and bind to the same recognition sequence but are isolated from different microbial sources. Restriction endonuclease isoschizomers may or may not cleave in the exact location as the restriction endonuclease with which it is being compared.

Modification methylase isoschizomer. A modification methylase isoschizomer is a term used to designate a group of modification methylase$ that recognize the same recognition sequence but are isolated from different microbial sources. Modification methylase isoschizomers may or may not chemically modify the same nucleotides within the recognition sequence as the modification methylase with which it is being compared.

Recognition sequence. Recognition sequences are particular sequences which restriction endonucleases and modification methylases recognize and bind along the DNA molecule. Recognition sequences are typically four to six (and in some cases eight) nucleotides in length with a two fold axis of symmetry.

Recombinant host. Any prokaryotic or eukaryotic microorganism which contains the desired cloned genes on an expression vector, cloning vector or any DNA molecule.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter A. DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein means that the promoter controls the initiation of the expression of the polypeptide encoded by the structural gene.

Expression. Expression is the process by which a gene produces a polypeptide. It involves transcription of the gene into messenger RNA (mRNA) and the translation of such mRNA into polypeptide(s)

Substantially pure. As used herein means that the desired purified enzyme is essentially free from contaminating cellular components which are associated with the desired enzyme in nature. Contaminating cellular components may include, but are not limited to, phosphatases, exonucleases or undesirable endonucleases.

DETAILED DESCRIPTION OF THE INVENTION

The standard method for cloning restriction endonuclease genes and genes of their DNA-protecting methylases relies on the proximity of the two genes to each other and on the expression of both genes in the host cell such as *E. coli.* First, a library is constructed by ligating fragmented genomic DNA from the source organism into a vector. For this library, one chooses a vector having one or, preferably more recognition sites of the restriction enzyme one wishes to clone. Generally, partial digestion conditions of the genomic DNA is used to prepare the library inserts, so as to avoid always cutting in the middle of a gene. Second, this library is transformed into and grown in a suitable host such as *E. coli.* Vector DNA that is then isolated from these transformed and grown cells is called the plasmid library. The plasmid library isolated is a mixture of different DNA molecules, having virtually all possible inserts and thus is representative of most if not all DNA sequences contained by the source organism. The vector/insert combinations having a methylase gene will have methylated the recognition sequences within the vector/insert DNA and the host chromosomal DNA if the methylase is expressed in the host used, preferably *E. coli.*

The isolated plasmid library DNA is then digested with the restriction enzyme. Unmethylated vector/insert combinations are degraded and methylated combinations survive the endonuclease treatment. The endonuclease-treated DNA is then transformed into a fresh host cell. Degraded combinations do not become established. Methyl-protected combinations, which survived the endonuclease treatment, can establish and maintain themselves in the new *E. coli* host cells, thereby forming clones.

Cell extracts of these clones are then assayed for restriction endonuclease activity in order to identify clones which express the desired restriction enzyme. Thus, genes for a methylase-restriction system can be cloned on a single recombinant DNA molecule, the restriction endonuclease being used to select DNA molecules carrying the gene of its corresponding methylase.

There are a number of reasons why the above method might not work with a particular endonuclease-methylase system. (1) The two genes (methylase and endonuclease) may not be closely linked. In that case both genes cannot be on the same DNA fragment insert. (2) The cloned fragment may, by chance, contain only methylase gene. A closely linked endonuclease gene might be inactivated by being cut by the restriction enzyme that generated the DNA fragment. Similarly, the methylase and endonuclease genes may have been separated from each other by a cut at an intervening restriction site. (3) The level of expression of the endonuclease may be high relative to the expression level of the methylase. In this situation, before the expressed methylase can protect the host DNA, the expressed endonuclease destroys the vector/insert combination as well as degrade the chromosome(s) and may kill the host cell. Alternatively, deletion(s) resulting in loss of part or all of the endonuclease gene from the vector/insert combination may allow the host to survive. (4) The methylase gene may not be expressed in the new host, leading to lack of protection of DNA from the endonuclease. (5) The endonuclease gene may not be expressed in the new host. In situations (1) and (3), if the endonuclease is expressed in the host, there will be no methylase enzyme activity to protect DNA in the host cell and the attempt to clone the endonuclease would fail.

The present invention is based on the discovery that for the KpnI restriction-modification system, the above standard methods for cloning restriction genes do not work. One must first express KpnI methylase in the host, herein exemplified by *E. coli*. before attempting to introduce a recombinant DNA molecule carrying a KpnI endonuclease genes. Furthermore, we have discovered that the KpnI endonuclease gene is closely linked to its corresponding methylase gene. The location of a DNA fragment carrying KpnI endonuclease gene was identified by hybridization techniques detailed below.

I. Isolation of the Genes Encoding for the KpnI Restriction Endonuclease and Modification Methylase or Isoschizomers thereof The overall strategy for reproducing this invention is as follows. Genes encoding for the KpnI restriction-modification system can be isolated from any strain of *Klebsiella pneumoniae* producing KpnI enzyme. Genes encoding for isoschizomers of KpnI or methylase isoschizomers of KpnI methylase may be obtained from any genus including, but not limited to, Arthrobacter, Bacillus, Citrobacter, Enterobacter, Escherichia, Flavobacterium, Haemophilus, Klebsiella, Micrococcus, Neisseria, Nocardia, Pseudomonas, Salmonella, and Streptomyces. The preferred genus to isolate isoschizomeric genes of the modification methylases and restriction endonucleases of the present invention is Klebsiella. The preferred strain to isolate genes encoding for KpnI restriction-modification system is *Klebsiella pneumoniae* strain BRL 25. BRL 25 has been deposited on Mar. 8, 1990, with the American Type Culture Collection, 12301 Parklawn Drive, Rockville, Maryland 20852, as ATCC 55014.

It is understood in this invention that genes encoding for isoschizomers of the restriction endonucleases and modification methylases of the present invention may be obtained from any organism including the genus Klebsiella by using the recombinant techniques described herein.

a. Methods for Cloning and Expressing

The isolated DNA which contains the KpnI restriction-modification genes or isoschizomers thereof is used to construct a recombinant DNA library in a vector. This library is then transformed and grown in a host, preferably *E. coli*. Finally, bulk insert/vector DNA combinations called the plasmid library are isolated from the host cells. Any host cell may be used in the present invention, provided that the KpnI restriction and modification genes or isoschizomeric genes thereof are expressed in said host. It is important to note that the vector must have at least one KpnI recognition site which the methylase may protect during the in vitro KpnI enzymatic digestion selection step.

A portion of the plasmid library is then digested with KpnI. Exonuclease and/or phosphatase may also by added to the digestion to enhance the destruction of non-methylated plasmids. The resulting mixture is then transformed into fresh host cells. Clones are picked and DNA from these clones are screened for resistance to digestion by KpnI. Clones having chromosomal and/or vector DNA that is not degraded by KpnI endonuclease indicates that the vector carries the KpnI methylase or isoschizomer thereof on the insert/vector combination. Other methylase screening methods include a methylation assay, i.e., the cell extract from the clone may be prepared and assayed in vitro for methylase activity (methylase protection and radioactive labelling).

As mentioned, we discovered that the KpnI endonuclease gene is closely linked to its corresponding methylase gene and that the two genes may be isolated on a single DNA fragment. However, the *E. coli* host selects for vectors lacking, e.g. deleted for the endonuclease gene. Thus, the resulting clones which expressed KpnI methylase did not express KpnI endonuclease. Isoschizomers of KpnI restriction and modification genes may be selected using the standard cloning procedure. Thus, at this point in the selection, it may be possible to obtain clones which express isoschizomeric methylase and restriction genes of KpnI.

Identification of clones which express the KpnI endonuclease gene can be accomplished by using well know colony hybridization techniques, provided that the host which is transformed with the library DNA already contains and expresses the KpnI methylase gene (protected host). Isolation of isoschizomeric genes of KpnI which require the use of a protected host for cloning these genes may be accomplished using this hybridization technique, as long as the isoschizomeric genes coding for the restriction and modification enzymes are closely linked.

In this selection technique, DNA sequences which flank and are closely linked to the methylase gene sequence contained by the protected host can be used as hybridization probes to select sequences contiguous to the methylase gene. The probe to be used for screening must be located close to the methylase gene but, to avoid cross-hybridization, cannot overlap with the methylase sequences contained by the protected host.

Briefly, a DNA fragment which contains the methylase gene but lacks the probe sequence is isolated and subcloned into a vector compatible with the vector used to construct the original DNA library. For example, a pBR322 derivative containing the methylase gene is compatible (able to replicate in the same host as another vector ) with a pCP13 vector library. A host containing this DNA fragment and expressing the methylase gene (protected host) is selected and then transformed with the library DNA. To prevent deletions of the KpnI restriction gene, it is important that the library DNA not be previously transformed into an unprotected host. For example, the ligated vector/genomic DNA is directly transformed into the protected host rather then transforming the protected host with the plasmid library that was previously isolated from an unprotected host. The protected hosts containing the vector/insert combination are then hybridized to the probe sequence described above. In the way, clones containing random inserts within and near the methylase gene can be obtained. Thus, since Applicants have discovered that the KpnI restriction and methylase genes are closely linked, selection of DNA fragments which hybridize to the probe may contain and express the KpnI restriction gene. Clones are then assayed for KpnI endonuclease activity to identify those which express KpnI restriction enzyme. Restriction endonuclease assays may be carried out as follows: (a) The cell extract for the clone may be prepare and assayed in vitro for its ability to digest substrate DNA, such as Ad-2. Cleavage of Ad-2 DNA indicates the presence of cloned restriction endonuclease; and (b) the cells themselves may be tested in vivo for their ability to resist phage infection. Resistance to phage infection indicates the presence of the restriction endonuclease.

Another approach for cloning a restriction enzyme gene is to isolate the protein, obtain an amino acid sequence for at least a portion of it, derive a corresponding nucleic acid sequence, synthesize a nucleic acid probe having this sequence, and using that probe to clone the gene. For example, oligonucleotide probes corresponding to the amino-terminal sequence of purified KpnI restriction enzyme may be used to identify clones carrying the restriction endonuclease gene. Alternatively, once the KpnI methylase and/or restriction genes are cloned, these gene sequences or synthetic oligonucleotides of these sequences may be used in hybridization experiments to obtain clones which contain these genes. Furthermore, one of ordinary skill in the art, using standard hybridization techniques, can utilize these sequences to isolate genes which encode for isoschizomers of the KpnI restriction and modification enzymes by altering the hybridization stringencies.

b. Methods for Enhancing Expression

Finally, one may wish to optimize expression of the KpnI endonuclease gene or isoschizomers thereof. Use of promoters that are inducible can express high levels of a heterologous structural gene's product is well known. Similarly use of high copy-number vectors to achieve high levels of gene expression is well known to the art. Vectors having an inducible high copy-number are especially useful, as is well known in the art. Note that expression in *E. coli* of the KpnI endonuclease promoter can be very strong and that no special expression strategy is necessary.

II. Isolation and Purification of the Restriction Endonuclease and Modification Methylase Enzymes from Recombinant Hosts The enzymes of this invention (KpnI and KpnI methylase) or isoschizomers thereof are preferably produced by fermentation of the recombinant host containing and expressing the cloned restriction endonuclease and/or modification methylase genes. The recombinant host, such as *E. coli* producing the cloned proteins, can be grown and harvested according to techniques well known in the art.

Any nutrients that can be assimilated by the host containing the cloned restriction endonuclease and modification methylase genes may be added to the culture medium. Glucose, sucrose, maltose, lactose, glycerol, ethanol, lactates, various fats and oils, and others may be used as carbon source, while yeast extract, peptone, defatted soybeans, corn steep liquor, bouillon and others are suitable as nitrogen source. Minerals and metal salts, e.g., phosphates, potassium salts and magnesium salts, iron, as well as vitamins and growth-promoting substances, may also be added as required.

Optimal culture conditions should be selected case by case according to the strain used and the composition of the culture medium. Restriction endonucleases and modification methylases produced by the recombinant hosts of this invention are accumulated inside the microbial cells.

The recombinant host cells producing the restriction endonuclease and/or modification methylase of this invention can be separated from the culture liquid, for example, by centrifugation. Both of these enzymes can be extracted and purified by using known protein purification techniques commonly employed for these types of enzymes.

In general, the collected microbial cells are dispersed in a suitable buffer, and then broken down by ultrasonic treatment to allow extraction of the enzyme by the buffer solution. After removal of the residue by ultracentrifugation, ammonium sulfate can be added to the supernatant of the crude lysate for salting out, and the precipitate which separates out is dissolved in a Tris-HCl buffer (pH: 7.5) and dialyzed against a buffer of the same composition. The dialyzed sample can be purified by ion-exchange chromatography, molecular-sieve chromatography and affinity chromatography, giving the restriction endonuclease or modification methylase of this invention.

In an example to purify KpnI from a recombinant host expressing the genes encoding for the restriction-modification system of KpnI, the crude lysate (after the cells are sonicated) is precipitated with streptomycin sulfate and the supernatant is then precipitated with ammonium sulfate. After ammonium sulfate precipitation, the precipitate which separates out is dissolved in a Tris-HCl buffer (pH: 7.5) and dialyzed against a buffer of the same composition. The dialyzed sample is then absorbed onto a heparin agarose column, followed by a 0.2 mM NaCl wash and then eluted with 0.2 to 0.8 M NaCl gradient. The active fractions were further purified by adsorption on a Mono-Q column using a gradient of 80 to 480 mM potassium chloride, affording a standard sample of KpnI. Column buffers used during the purification of KpnI contained 20 mM Tris-HCl (pH 7.5), 0.1 mM EDTA and a reducing agent (Dithiothreitol or $\beta$ mercaptoethanol).

According to the present invention, assays to detect the presence of the restriction endonucleases and modification methylases can be used during the conventional biochemical purification methods to determine the presence of these enzymes.

Restriction endonuclease can be identified on the basis of the cleavage of its recognition sequence. As substrate, there can be used, for example, Adenovirus-2 (Ad-2) DNA. The DNA fragments obtained are separated electrophoretically in agarose gels in the buffer systems conventional for the fragment separation in the presence of ethidium bromide.

Demonstration of modification methylase activity can be, but is not limited to, a two-step identification process. First, DNA substrate (Ad-2 DNA) that contains the recognition sequence is incubated with column fractions to be tested for methylase activity. Secondly, this DNA is then challenged with the corresponding restriction activity to identify those fractions which contain methylase activity. For example, while assaying for KpnI methylase, the DNA samples will be challenged with KpnI. Thus, DNA samples which do not exhibit cleavage with KpnI contain KpnI methylase activity.

EXAMPLES

Example 1: Experimental

Example 1.1: Materials and Methods

Ad-2, adenovirus-2; Ap, ampicillin; bp, base pair(s); EtdBr, ethidium bromide; kbp, 1000 base pairs (bp); IPTG, isopropylthio-beta-galactoside; Km, kanamycin; PolIK, Klenow (large) fragment of *E. coli* DNA polymerase I; $^R$, resistance; $^S$, sensitivity; SDS, sodium dodecyl sulfate; Sp, spectinomycin; Tc, tetracycline; and X-Gal, 5-bromo-4-chloro-3-indolyl-beta-D-galactoside.

Example 1.2: Bacterial Strains and Growth Conditions

*Klebsiella pneumoniae* BRL 25 producing KpnI restriction endonuclease was grown in a 15 l fermentor at 37° C. to mid-log phase in nutrient media (pH 7.2) consisting of 10 g/l Ardamine Z, 15 g/l NZ amine, 5 g/l NaCl, 12.1 g/l Sigma 7-9, and 10 g/l cellulose. These cells were centrifuged and stored at −70° C. as a cell pellet prior to total genomic DNA isolation.

*E. coli* strains were grown at 37° C. in YET broth (5 g/l yeast extract, 10 g/l tryptone, and 5 g/l NaCl with antibiotic supplements of 100 mg/l ampicillin; 20 mg/l tetracycline; 50 mg/l spectinomycin; and 50 mg/l kanamycin; as appropriate. *E. coli* strains K802 (Maniatis T et al. (1982) *Molecular Cloning a laboratory manual.* Cold Spring Harbor Laboratory, Cold Spring Harbor, New York) and BRL 2380, werer used interchangeably for cloning the KpnI genes. BRL 2380 is a recAI$^-$, endA$^-$, phi80dlacZdeltaM15 derivative of MCI061 (Casadaban MJ and Cohen SN (1980) J. Mol. Biol. 138:179-207). Competent *E. coli* strains were either obtained from BRL or made by a protocol described by Hanahan D (1983) J. Mol. Biol. 166:557-580.

Example 1.3: Vectors/Plasmids

Because a methylase protection scheme was to be used to clone KpnI restriction and modification genes, it was necessary to use vectors containing KpnI recognition site(s) (FIG. 1). Plasmid pCP13lacZ, containing a single KpnI site, was constructed from the cosmid pCP13 (Darzins A and Chakrabarty AM (1984) J. Bacteriol. 59:9-18) by replacing two adjacent small EcoRI fragments (700 bp and 1800 bp) of pCP13 with the 445 bp HaeII fragment (blunt ended with T4 DNA polymerase) of pUC19 (Yanisch-Perron C et al. (1985) Gene 33:103-109) containing the lacZ gene. Plasmid pBR322Km, containing two KpnI sites and a Km$^R$ gene flanked by KpnI sites, was constructed as follows: First, pBR322lacZ, containing a KpnI site, was made from pBR322 (Bolivar F et al. (1977) Gene 2:95-113) by substituting the 1,427 bp EcoRI/AvaI Tc$^R$ gene of pBR322 with the 445 bp lacZ fragment described above. Then plasmid pUC19Km, having a unique KpnI restriction site adjacent to the amino-terminus of the Km gene, was constructed by inserting the small ScaI/-BamHI Km gene (blunt-ended with PolIK) of pKT240 (Bagdasrian MM et al. (1983) Gene 26:273-282) into the SmaI site of pUC19. The final construct, pBR322Km, was obtained by ligating the PolIK-treated EcoRI/-BamHI Km fragment of pUC19Km into the SmaI restriction site of pBR322lacZ.

Example 1.4: DNA Isolations

Small scale plasmid DNA isolations were performed by an alkaline lysis method (Maniatis et al., supra). For large scale preparations, alkaline lysis was followed by a standard CsCl-ethidium bromide (EtdBr) gradient centrifugation.

*K. pneumoniae* total genomic DNA was isolated by resuspending 2 grams of frozen Klebsiella cells in 8 ml of TNE buffer (50 mM Tris-HCl, pH 8.0, 50 mM NaCl, and 10 mM EDTA (ethylene diamine tetraacetic acid)). A 10 mg/ml lysozyme solution in TNE buffer was added to the cell suspension to a final concentration of 1 mg/ml. After a 1 hr incubation at 37° C., 10% SDS was added to a 2% final concentration and the suspension was shaken gently until lysis was complete. After cell lysis, the lysate was extracted once with phenol and twice with phenol:chloroform:isoamyl alcohol (25:24:1). DNA was spooled with a glass rod under two volumes of cold EtOH. The spooled DNA was dissolved in TE (10 mM Tris-HCl, pH 8.0, and 1 mM EDTA) and purified by CsCl-EtdBr gradient centrifugation.

Example 1.5: Colony and Southern Hybridization

Colony and Southern Hybridizations were performed essentially as described (Maniatis et al., supra) except that prehybridization solutions lacked SDS, 5×SSPE (standard saline phosphate/EDTA; 1× =50 mM NaCl, 10 mM sodium phosphate, pH 7.4, 1 mM EDTA) was substituted for 5×SSC (standard saline citrate; 1×50 mM NaCl, 15 mM sodium citrate, pH 7.0) and 150 mg/l of salmon sperm DNA was included. Appropriate DNA fragments to be labeled were purified from agarose gels using a Gene-Clean ™ kit supplied by Bio 101 (La Jolla, California). Purified fragments (about 0.2 to 0.5 µg) were labeled with a nick-translation kit (BRL) using [α-$^{32}$P]dCTP. Hybridizations were performed at 65° C.

Example 1.6: Construction of Genomic Libraries

A cosmid library was constructed based on pCP13lacZ. pCP13lacZ DNA was digested with BamHI and dephosphorylated using calf intestine alkaline phosphatase (Boehringer Mannheim). Genomic DNA of *K. pneumoniae* was digested partially with Sau3AI. Two µg of cosmid vector DNA was ligated with 2 µg of chromosomal DNA using 2 units of T4 DNA ligase in 1×ligase buffer (BRL) overnight at room temperature. One fourth of the ligated DNA was packaged using Stratagene's Gigapack Gold ™ Lambda Packaging System and transfected into K802. Approximately $9 \times 10^4$ Tc$^R$ colonies were pooled and an aliquot was inoculated into 1 l of YET media containing tetracycline. After a 5 hour growth, the cells were harvested and plasmid DNA was purified as described above.

A plasmid library was constructed based on pBR322Km by ligating 1 µof BamHI cleaved and dephosphorylated pBR322Km with 0.1 to 0.2 µg of 2-8 kb fragments of *K. pneumoniae* genomic DNA produced by partial digestion with Sau3AI and purified from an agarose gel. Plasmid DNA was prepared as described above from 1 l of cells grown in the presence of kanamycin and ampicillin.

Example 1.7: Selection of Clones Expressing Methylase and Endonuclease

Clones expressing KpnI methylase were selected by digesting 6 µg of pBR322Km library DNA overnight with 200 units of KpnI. The digested DNA was dephosphorylated, extracted with phenol:chloroform:isoamyl alcohol, and ethanol precipitated. One half of the digested DNA was used to transform *E. coli* K802 competent cells. A second round of selection was performed by isolating plasmid DNA from half of the Km$^R$ colonies, digesting the DNA as above, and transforming K802 cells with 1 µg of KpnI digested DNA. Plasmid DNA isolated from clones selected on plates containing kanamycin and ampicillin was tested for resistance to KpnI. (Selection with kanamycin alone often resulted in the isolation of deletions.) Protection of the resident plasmid and the host chromosomal DNA from digestion with KpnI indicated the presence of methylase activity.

Figure 2:
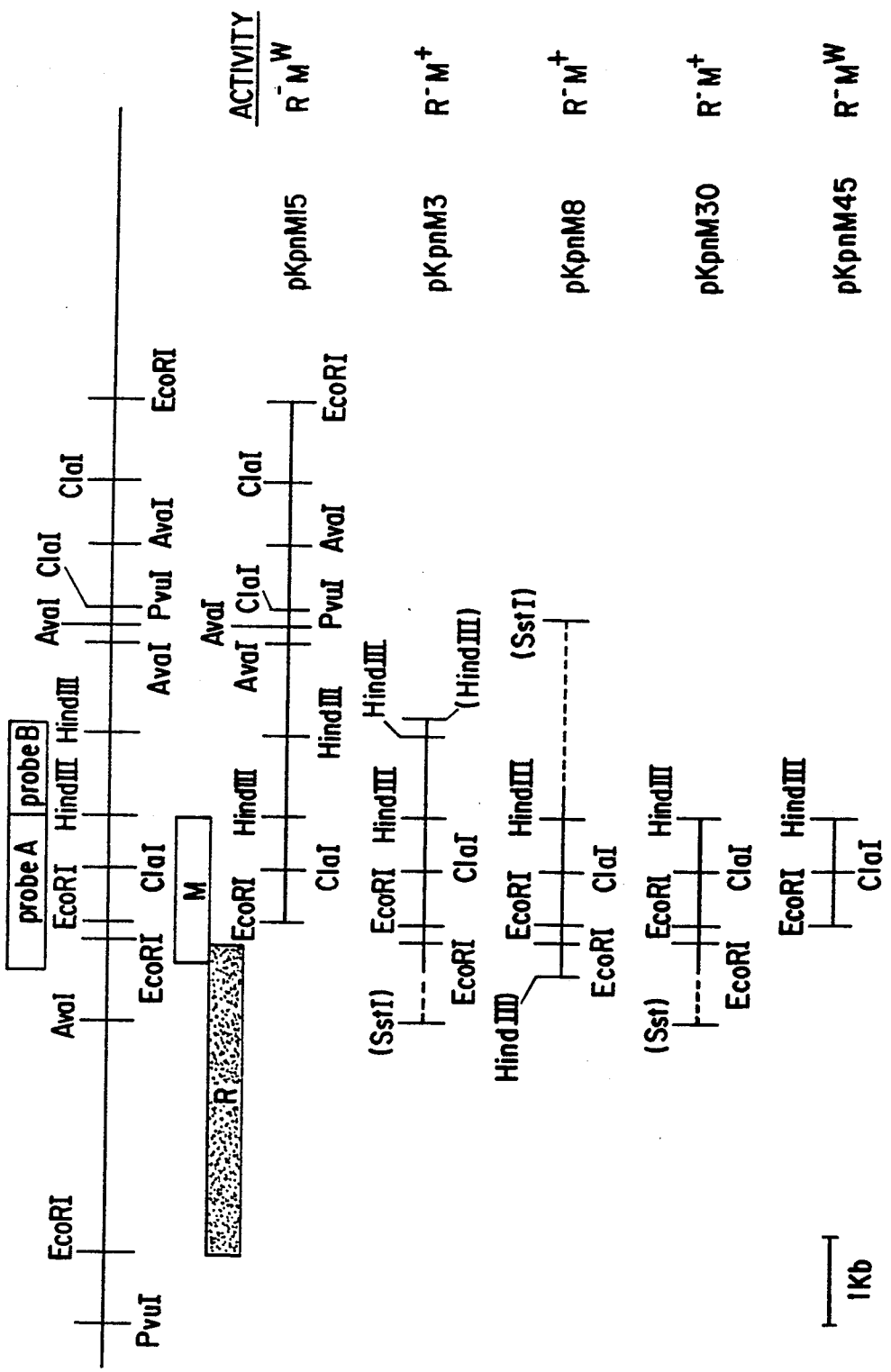
FIG. 2 presents a restriction map of K. pneumoniae DNA in the region of the KpnI restriction (R) - modification (M) system. Methylase clones pKpnM3, pKpnM8 and pKpnM30 are derivatives of pBR322Km while pKpnM15 and pKpnM45 are derived from pBR322lacZ. Broken lines represent inserts non-homologous to the regions of interest which were the result of a ligation event joining two or more fragments during library construction. Restriction sites within parentheses are derived from the vector. Probe A was generated from the about 2.2 kb SstI/HindIII fragment of pKpnM3 or the about 1.8 kb HindIII fragment of pKpnM8. Probe B was the about 0.9 kb HindIII fragment derived from pKpnM3. The restriction and methylation phenotypes based upon Protection of plasmid and genomic DNA isolated from an E. coli host carrying the designated plasmid are shown: (+) enzyme activity present; (−) no activity; and (W) partial or weak activity.

Selection of KpnI endonuclease clones required the use of a protected host expressing KpnI methylase. The pCP13lacZ cosmid library packaging mix was transfected into BRL 2380 containing pKpnM30 (FIG. 2). $Ap^R Tc^R$ colonies were hybridized with a probe (probe B) derived from sequences located adjacent to the methylase gene but having no homology to pKpnM30. Positive clones were subsequently tested in vitro for restriction enzyme activity.

Example 1.8: Assay for Restriction Enzyme

Overnight cultures (20 ml) were harvested and resuspended in 1 ml buffer containing 10 mM Tris-HCl (pH 7.5), 10 mM beta-mercaptoethanol and I mM EDTA. Cells were sonicated on ice by three or four 10 second blasts with a microtip probe. Adenovirus-2 DNA substrate (1.0 μg) was digested in 1×BRL REact TM 4 buffer with serial dilutions of extract for 1 hour at 37° C. DNA was fractionated by electrophoresis and visualized by EtdBr staining.

Examples 2-8: Result and Discussion

Example 2: Identification of Methylase Clones

Since the selection for KpnI methylase is dependent upon methylation of the KpnI restriction sites in the cloning vector, pCP13 and pBR322 were modified to contain one and two KpnI recognition sites, respectively (Example 1.3). A plasmid library of *K. pneumoniae* DNA in pBR322Km (FIG. 1) was subjected to two rounds of KpnI digestion to minimize the background of clones lacking the gene for KpnI methylase. A potential problem in the use of this selection process is that loss of KpnI site(s) in the vector due to deletions increases the background of clones not containing the KpnI methylase. Consequently, a double antibiotic selection was used which increased the proportion of clones expressing KpnI methylase. Indeed, plating 1 μg of library DNA on plates containing Km as the only selection yielded over one million survivors, while an identical plating on plates containing Km and Ap gave approximately 1600 surviving colonies. When plasmid DNA was isolated from $Km^R Ap^R$ clones surviving the enrichment procedure, 18 out of 20 expressed methylase as judged by resistance to KpnI restriction of the host DNA, but no clones exhibited endonuclease activity. Two clones, pKpnM3 and pKpnM8, containing a 3.5 kb and 4.0 kb insert, respectively, were used for further study (FIG. 2).

Example 3: Subcloning of the KpnI Methylase Gene

Both pKpnM3 and pKpnM8 were mapped with various restriction enzymes in order to localize the methylase gene. A 2 kb overlap was found when resulting restriction maps of were compared (FIG. 2). The 2.2 kb SstI-HindIII fragment of pKpnM3 was subcloned into pBR322lacZ vector to generate pKpnM30. pKpnM30 expressed KpnI methylase as determined by the protection from KpnI restriction of plasmid and chromosomal DNA isolated from cells harboring pKpnM30. A deletion derivative, pKpnM45, missing the EcoRI and EcoRI-SstI fragments from pKpnM30 (FIG. 2), appeared to retain only partial methylase activity. DNA isolated from a host containing pKpnM45 was only 40% to 50% resistant to digestion with KpnI. These experiments localized the gene for KpnI methylase to a 1.7 kb region shown in FIG. 2.

Example 4: Attempts to Clone the KpnI Endonuclease Gene in an Unprotected Host As discussed, the majority of endonuclease and methylase genes of restriction-modification systems are closely linked. In order to identify representative clones spanning the genome regions adjacent to the methylase gene, methylase clones with larger inserts in a pCP13lacZ cosmid library (Example 1.6) were tested in an attempt to isolate a clone containing a linked gene for KpnI endonuclease. Cosmid library DNA (5 μg) was digested with an excess of KpnI, dephosphorylated, and transformed into K802 cells. Plasmid and chromosomal DNA from ten survivors were digested with KpnI restriction enzyme. Eight survivors yielded plasmid DNA resistant to KpnI digestion. However, chromosomal DNAs from these survivors were not resistant to digestion with KpnI. Therefore, selection of these clones was due to the loss of the KpnI site in the vector rather than the presence of genes expressing methylase. To eliminate these false positives, 70 transformants were hybridized with probe A derived from pKpnM3 (FIG. 2). Three positive clones M10, M55 and M65 were subsequently assayed for methylase and endonuclease activities as described in Examples 1.7 and 1.8, respectively. All three clones exhibited methylase but lacked endonuclease activity. As will be shown below, all three cosmid clones contained deletions in the region of the *K. pneumoniae* genome corresponding to the gene coding for KpnI endonuclease.

Example 5: Chromosomal Localization the KpnI Endonuclease Gene

The *K. pneumoniae* genome contiguous to the KpnI methylase gene was mapped to identify which regions were present or missing in the cosmid clones M10, M55 and M65. Southern blot analysis of EcoRI digested *K. pneumoniae* chromosomal DNA demonstrated homology of probe A (pKpnM8) to three fragments of about 0.2 kb, 3.5 kb, and 6 kb in length. Mapping of pKpnM3 and pKpnM8 (FIG. 2) placed the location of the 0.2 kb EcoRI fragment in the KpnI methylase gene. Because probe A hybridized with sequences adjacent to this reference point, EcoRI sites must be located 6 kb and 3.5 kb on either side of the 0.2 kb fragment.

Initially, the 6.0 kb EcoRI fragment was cloned into pBR322lacZ. EcoRI digested *K. pneumoniae* DNA was purified from the 6 kb region of an agarose gel, ligated to EcoRI cleaved pBR322lacZ and transformed into BRL 2380 cells. Plasmid DNA, isolated from 950 $Ap^R$ colonies, was digested with KpnI and used to transform *E. coli* BRL 2380 cells. Eighteen of the 130 $Ap^R$ survivors hybridized with probe A (pKpnM8) and contained the 6 kb EcoRI insert. The methylase activity in cells bearing these plasmids protected only about 40 to about 50% of the plasmid and chromosomal DNA from KpnI digestion. None of these isolates expressed endonuclease activity. One of the clones with a 6 kb EcoRI fragment, designated pKpnM15, was mapped (FIG. 2). Comparison of overlapping sequences of pKpnM15 with pKpnM3 and pKpnM8 lead to the conclusion that the 6 kb EcoRI fragment is located to the right of the methylase gene (FIG. 2).

Initial attempts to clone in lambda gt10 (Huynh TV et al. (1985) in *DNA cloning: a practical approach.* ed.: Glover D, IRL Press, McLean, VA. pp 49-78) the 3.5 kb EcoRI fragment, which must be located to the left of the methylase gene, were unsuccessful. Plaques of lambda gt10 that hybridized to probe A (pKpnM8) contained large deletions in the 3.5 kb EcoRI insert. In addition, examination of the cosmid clones M10, M55, and M65, which were made in an effort to pick up regions of the genome contiguous to the KpnI methylase gene, revealed partial deletions of the 3.5 kb EcoRI fragment, even though the 6.0 kb and 0.2 kb EcoRI fragments remained intact. Failure to clone a stable 3.5 kb EcoRI fragment suggested the presence in this fragment of a functional gene for KpnI endonuclease and-/or other lethal gene(s). If the endonuclease gene is present, it is reasonable to assume that previous attempts to clone both genes on a common fragment resulted in isolation of deletions of the endonuclease gene. To establish in an E. coli host a plasmid expressing both a restriction and modification gene, methylation of the host DNA must precede endonuclease digestion. Evidently, the KpnI restriction-modification system cloned in E. coli did not exhibit this coordinated expression. Therefore, utilization of a host protected with the KpnI methylase would circumvent this problem. Therefore, the 3.5 kb EcoRI fragment was cloned in such a host.

Example 6: Cloning of the KpnI Endonuclease Gene in a Protected Host

E. coli BRL 2380 containing pKpnM30 (FIG. 2) was transfected with a cosmid library in pCP31acZ containing Klebsiella pneumoniae DNA partially digested with Sau3AI (Example 1.6). To prevent deletions of the KpnI endonuclease gene, DNA was packaged and transfected directly into a protected host rather than transforming the protected host with a cosmid library previously passed through an unprotected host. The 860 $Ap^R Tc^R$ transformants obtained were subjected to colony hybridization using probe B derived from the HindIII fragment of pKpnM3 (FIG. 2). This probe has no homology to pKpnM30, but was localized to the region of interest. Therefore, it was used to identify cosmid clones with large chromosomal inserts that might contain the endonuclease gene. Colonies which hybridized to probe B were then tested for KpnI endonuclease activity. Three clones (AH3, AH4, and AH13) out of the eight tested exhibited KpnI restriction endonuclease activity. Plasmid DNA isolated from two of these clones (AH3 and AH4) contained the 3.5 kb EcoRI fragment as expected. The cosmid isolated from AH3 containing the KpnI restriction and methylase genes was designated, pCP13RMKpnI.

The 3.5 kb EcoRI fragment was subcloned into a derivative of the runaway plasmid, pJJS1010 (Sninski JJ et al. (1981) Gene 16:275–286), using E. coli BRL 2380 containing pKpnM30 as a host. (The modification of pJJS1010 involved insertion of an SP6 promoter. This change is believed to not affect expression levels in this construction, i.e., unmodified pJJS1010 would have given identical results.) The strain containing both plasmids, designated AH29, produced greater than $1 \times 10^7$ units of KpnI endonuclease per gram of wet cells, which is several thousand fold greater than that produced by K. pneumoniae.

Example 7: Establishment of Stable KpnI Endonuclease and Modification Genes in E. coli In the above Examples, the KpnI endonuclease and methylase genes were maintained and expressed in E. coli on different plasmids. In a production setting, one would prefer to have both genes on a single plasmid. Therefore, the KpnI methylase gene was subcloned on a $Km^R$ derivative of pPM103 (Sninski, supra), designated pPM103Km, which contains a temperature sensitive origin of replication. DNA of plasmid pCP13RMKpnI, having both the KpnI endonuclease and methylase genes, was isolated from AH3 (Example 6). This DNA was then introduced into BRL 2380 protected with KpnI methylase expressed on pPM103Km. Maintaining tetracycline selection without kanamycin, cultures were incubated at a non-permissive temperature (42° C). Plasmid preparations of two $Km^S Tc^R$ colonies, designated RM6 and RM10, contained pCP13RMKpnI, but lost pPM103Km and its KpnI methylase gene. These $Km^S Tc^R$ clones subsequently tested positive for both endonuclease and methylase activity. The ability to maintain pCP13RMKpnI without continuous protection with a second plasmid expressing the methylase gene demonstrates the stability, after establishment in E. coli of the KpnI restriction-modification genes on a common DNA fragment.

Example 8: Sequencing of KpnI Endonuclease and Methylase Genes

FIG. 3 presents a sequence of the cloned region of DNA having the KpnI restriction endonuclease and methylase genes. Sites discussed in the text are generally indicated in bold.

The sequence as presented contains some questionable data so may not be adequate for gene splicing experiments which require accurate sequencing data. The sequence is estimated to be at least about 98% accurate, so is more than adequate to make oligonucleotide probes useful for identifying new recombinant DNA clones of these genes or for isolation of genes from other organisms which encode for restriction isoschizomers of KpnI as well as methylase isoschizomers of KpnI methylase.

The sequence extends from an AvaI site (designated nucleotides 1–6) to a HindIII site (currently numbered nucleotides 2311–2316). The presence of restriction sites has been experimentally verified for HincII (460–465), StyI (741–746), EcoRI (902–907 and 1169–1174), RsaI (1002–1005 and 1699–1702), and ClaI (1741–1746). Sequencing of 12 aminoterminal amino acids residues of KpnI restriction enzyme showed that the amino terminus of the mature endonuclease protein is encoded by the 5'CAT3' codon at nucleotides 836–838. (Since the endonuclease gene is oriented from "right to left" in FIG. 3, the initiation codon reads at 5'CAT3', the reverse complement of 5'AUG3'.) The translational initiation codon of the endonuclease is probably at nucleotides 836–838, though it might be at nucleotides 860–862. (The presence of a canonical ribosome binding site (5'AGGAGG3', present in FIG. 3 as its reverse complement, 5'CCTCCT3') at nucleotides 845–850 (not indicated by bold) argues for the former site.) The endonuclease structural gene is thought to extend to about nucleotide 200. The methylase structural gene is thought to extend from about nucleotide 1000 to about nucleotide 2100. (A possible translation initiation codon, 5'AUG3', is present at nucleotides 1006–108, just after a conanical ribosome binding site at nucleotides 996–1001 (neither indicated by bold)).

These data may be used by those of ordinary skill in the art to clone the KpnI genes from BRL 25 and express them in a heterologous host. The endogenous promoter is highly active in *E. coli* so need not be replaced. The methylase may be cloned without a complete, functional endonuclease gene either on an about 1.6 kb StyI/HindIII fragment or on an about 1.9 kb HincII/HindIII fragment. The two genes may be cloned together on an about 2.3 kb AvaI/HindIII fragment. The sequence provided in FIG. 3 can be used by those of ordinary skill in the art to design synthetic oligonucleotide probes useful for identifying which clone in a library contains the desired vector/insert combination using well know methods of molecular biology and genetic engineering. Furthermore, one of ordinary skill int eh art may use these synthetic oligonucleotide probes for identifying clones which contain genes encoding for restriction isoschizomers of KpnI.

Although the foregoing refers to particular preferred embodiments, it will be understood that the present invention is not so limited. It will occur to those of ordinary skill in the art that various modifications may be made to the disclosed embodiments and that such modifications are intended to be within the scope of the present invention, which is defined by the following claims.

What is claimed is:

1. A recombinant DNA molecule comprising a structural gene encoding a restriction endonuclease which recognizes the palindromic sequence:

5' G GTAC C 3'
3' C CATG G 5' wherein said endonuclease cleaves said sequence between the C residues, producing a four base 3' extension.

2. A recombinant DNA molecule comprising a structural gene encoding a KpnI restriction endonuclease which recognizes the palindromic sequence:

5' G GTAC C 3'
3' C CATG G 5' wherein said endonuclease cleaves said sequence between the C residues, producing a four base 3' extension.

3. A recombinant vector comprising a structural gene encoding a restriction endonuclease as in claim 1 or 2 operably linked to a promoter to express said gene.

4. The recombinant vector of claim 3 wherein said promoter is a KpnI endonuclease promoter.

5. A recombinant host expressing a gene encoding a restriction endonuclease as in claim 1 or 2.

* * * * *

UNITED STATES PATENT AND TRADEMARK OFFICE
CERTIFICATE OF CORRECTION

PATENT NO. : 5,082,784

DATED : January 21, 1992

INVENTOR(S) : Deb K. Chatterjee, et. al.

It is certified that error appears in the above-identified patent and that said Letters Patent is hereby corrected as shown below:

```
Column 3, lines 58-59, delete, "5' G GTAC C 3' and 3' C CATG G 5'" and
therefor insert -- 5' G GTAC^C 3' and 3' C^CATG G 5'--.
Column 3, line 63, change "(" " indicates" to read --("^" indicates--.
Column 3, line 67, change "endonuclea" to --endonuclease--.
Column 4, line 49, change "Protection" to --protection--.
Column 5, line 26, change "methylase$" to --methylases--.
Column 5, line 47, change "Promoter A." to Promoter. A--.
Column 8, line 22, change "know" to --known--.
Column 8, line 58, change "the" to --this--.
Column 8, line 68, change "prepare" to --prepared--.
Column 11, line 20, change "werer" to --were--.
Column 11, line 22, change "MCI061" to --MC1061--.
```

Column 12, line 45, please change "$\mu$of" to --$\mu$g of--.

Column 13, line 58, please delete "of".

Column 16, line 63, please change "108" to --1008--.

Column 17, line 11, please change "know" to --known--.

Column 17, line 13, please change "int eh" to --in the--.

UNITED STATES PATENT AND TRADEMARK OFFICE
CERTIFICATE OF CORRECTION

PATENT NO. : 5,082,784

DATED : January 21, 1992

INVENTOR(S) : Deb K. Chatterjee, et. al.

It is certified that error appears in the above-identified patent and that said Letters Patent is hereby corrected as shown below:

Column 18, claim 1, lines 4 and 5, please delete:

"5' G  GTAC  C 3'

3' C  CATG  G 5'"

and insert therefor:

--5' G  GTAC^C 3'

3' C^CATG  G 5'--.

Column 18, claim 2, lines 4 and 5, please delete:

"5' G  GTAC  C 3'

3' C  CATG  G 5'"

and insert therefor:

--5' G  GTAC^C 3'

UNITED STATES PATENT AND TRADEMARK OFFICE
CERTIFICATE OF CORRECTION

PATENT NO. : 5,082,784
DATED : January 21, 1992
INVENTOR(S) : Deb K. Chatterjee, et. al.

It is certified that error appears in the above-indentified patent and that said Letters Patent is hereby corrected as shown below:

3' C CATG G5'--.

Signed and Sealed this

Thirtieth Day of November, 1993

Attest:

BRUCE LEHMAN

*Attesting Officer*     *Commissioner of Patents and Trademarks*